(12) United States Patent
Dekel et al.

(10) Patent No.: US 8,923,580 B2
(45) Date of Patent: Dec. 30, 2014

(54) SMART PACS WORKFLOW SYSTEMS AND METHODS DRIVEN BY EXPLICIT LEARNING FROM USERS

(75) Inventors: Shai Dekel, Ramat-Hasharon (IL); Alexander Sherman, Herzliya (IL); Sohan Rashmi Ranjan, Bangalore (IN); Viswanath Avasarala, Niskayuna, NY (US); Xiaofeng Liu, Niskayuna, NY (US); Alexandre Nikolov Iankoulski, Niskayuna, NY (US); Tianyi Wang, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 483 days.

(21) Appl. No.: 13/303,714

(22) Filed: Nov. 23, 2011

(65) Prior Publication Data

US 2013/0129165 A1 May 23, 2013

(51) Int. Cl.
| | |
|---|---|
| *G06K 9/00* | (2006.01) |
| *G06K 9/62* | (2006.01) |
| *G06F 19/00* | (2011.01) |

(52) U.S. Cl.
CPC .................................. *G06F 19/321* (2013.01)
USPC ........................... 382/128; 382/155; 382/156

(58) Field of Classification Search
CPC ...... G06F 19/321; A61B 6/461; A61B 6/462; A61B 6/463; A61B 6/464; A61B 6/465; A61B 6/466
See application file for complete search history.

(56) References Cited

U.S. PATENT DOCUMENTS

| 7,525,554 B2 | 4/2009 | Morita et al. |
|---|---|---|
| 2007/0106633 A1* | 5/2007 | Reiner .............................. 707/1 |
| 2007/0282912 A1* | 12/2007 | Reiner ....................... 707/104.1 |
| 2008/0166070 A1 | 7/2008 | Kariathungal et al. |
| 2010/0080427 A1 | 4/2010 | Yeluri et al. |

OTHER PUBLICATIONS

Bersini et al., "Is readability compatible with accuracy? From neuro-fuzzy to lazy learning", Proceedings in Artificial Intelligence 7, C. Freksa, Ed. Berlin, Germany: Infix/Aka, pp. 10-25, 1998.

Bonissone et al., "Case-based reasoning, in Handbook of Fuzzy Computing," Section F4.3, Ruspini, Bonissone, Pedrycz (Eds.), Institute of Physics Publishers, 1998. (20 pages).

Bonissone et al., "Evolutionary Algorithms + Domain Knowledge = Real-World Evolutionary Computation," IEEE Transactions on Evolutionary Computation, 10(3): 256-280, Jun. 2006.

(Continued)

*Primary Examiner* — Nirav G Patel
*Assistant Examiner* — Timothy Choi
(74) *Attorney, Agent, or Firm* — Hanley, Flight and Zimmerman, LLC

(57) ABSTRACT

Certain embodiments of the present invention provide methods and systems for determining a hanging protocol for display of clinical images in a study. Certain embodiments provide a machine learning hanging protocol analysis system. The example system includes an image processing module to process image data to provide one or more features. The example system includes a learning engine to receive processed image data and additional data to learn and adapt a hanging protocol for repeated use by applying one or more machine learning algorithms to the processed image data and additional data. The learning engine is to continue to refine an available selection of candidate layouts based on the processed image data and additional data to provide one or more layout choices for selection to form a hanging protocol for display of image and other data.

14 Claims, 13 Drawing Sheets

(56) References Cited

OTHER PUBLICATIONS

Bowden et al., "NeuroNames Brain Hierarchy". NeuroImage 2 (1): 63-83, (Mar. 1995).
Bug et al., "The NIFSTD and BIRNLex vocabularies: building comprehensive ontologies for neuroscience." Neuroinformatics 2008, 6:175-194.
Chen et al., "Case-Based Reasoning System and Artificial Neural Networks: A Review, Neural Computing & Applications," vol. 10, Iss. 3, pp. 264-276, 2001.
Cortes et al., "Support-Vector Networks", Machine Learning, 20, 1995 (25 pages).
Criminisi et al., "Regression forests for efficient anatomy detection and localization in CT studies", MICCAI 2010 workshop MCV, 2011. (12 pages).
V. Dicken et al., "Rapid image recognition of body parts scanned in computed tomography datasets", Int. J. CARS, 5:527-535, 2010.
J. Feulner, et al., "Comparing axial CT slices in quantized N-dimensional SURF-descriptor space to estimate the visible body region", Computerized Medical Imaging and Graphics, 35:227-236, 2011.N.
N. Karssemeijer, "A statistical method for automatic labeling of tissues in medical images", Machine Vision and Applications, 1990. 3:75-86.
Khan et al. "Achieving self-configuration capability in autonomic systems using case-based reasoning with a new similarity measure." Communications in Computer and Information Science, Springer Berlin Heidelberg, 2:97-106, Aug. 2007. (10 pages).
C. Lee, et al., "Identifying multiple abdominal organs from CT image series using a multimodule contextual neural network and spatial fuzzy rules", IEEE Trans. Info. Tech. Biomed. 7(3) 208, 2003.
X. Liu, et al., "Abdominal multi-organ localization on contrast-enhanced CT based on maximum a posterior probability and minimum volume overlap", IEEE ISBI 2011 (4 pages).
X. Liu et al., "Organ labeling using anatomical model-driven global optimization", 2011 HISB. (8 pages).
K. Nakamura, et al., "A machine learning approach for body part recognition based on CT images", SPIE Medical Imaging 2008 (9 pages).
R. Kohavi, Ron, "A study of cross-validation and bootstrap for accuracy estimation and model selection". Proceedings of the Fourteenth International Joint Conference on Artificial Intelligence 2, 1995. (7 pages).
Yao and Summers, "Statistical Location Model for Abdominal Organ Localization," Med Image Comput Comput Assist Interv. 2009; 12(Pt 2):9-17.
Rosse, JVL Mejino 2003. A reference ontology for biomedical informatics: the Foundational Model of Anatomy. J Biomed Inform. 36:478-500.
Yao et al., "Simultaneous location detection of multi-organ by atlas-guided eigen-organ method in volumetic medical images", Int. J. Comp. Assist. Radiol., Surg. 1, 42-45, 2006.
Yao et al, "Statistical location model for abdominal organ localization", MICCAI 2009. (14 pages).
Christopher.M. Bishop, "Abstract from the book Neural Networks for Pattern Recognition," Oxford: Oxford University Press, 1995, retrieved from the internet http://dl.acm.org/citation.cfm?id=525960&preflayout=flat last visited on Aug. 30, 2012.

\* cited by examiner

SMART PACS WORKFLOW SYSTEMS AND METHODS DRIVEN BY EXPLICIT LEARNING FROM USERS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

The present invention generally relates to hanging protocol configuration in a picture archiving and communication system. In particular, certain embodiments of the present invention relate to machine learning based hanging protocol configuration in a picture archiving and communication system.

Healthcare environments, such as hospitals or clinics, include clinical information systems, such as hospital information systems ("HIS") and radiology information systems ("RIS"), and storage systems, such as picture archiving and communication systems ("PACS"). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

Current PACS systems use general techniques known as "hanging protocols" to format display or layout of images. Hanging protocols allow a user to display images based on modality, anatomy, and procedure. Hanging protocols present a perspective or view to a user, such as a radiologist. Images may be grouped according to characteristics such as DICOM series or series number.

Additionally, PACS systems attempt to prepare images for viewing by users by applying a series of processing steps or functions included in a hanging protocol referred to as a Default Display Protocol ("DDP"). A DDP is a default workflow that applies a series of image processing functions to image data to prepare the image data for presentation to a user on a particular monitor configuration. DDPs typically include processing steps or functions that are applied before any diagnostic examination of the images. A DDP may be based on a type of imaging modality used to obtain the image data, for example. In general, a DDP attempts to present image data in a manner most useful to many users.

Currently, a hanging or display protocol in PACS applications uses individual data elements of an image's DICOM header and HL-7 order information to classify a study type and determine how the study should be displayed.

BRIEF SUMMARY

Certain embodiments of the present invention provide methods and systems for determining a hanging protocol for display of clinical images in a study.

Certain embodiments provide a method to determine a hanging protocol for clinical image display. The example method includes monitoring, using a processor, user workflow in a first session. The example method includes accepting, using a processor, user input to record/teach at least a portion of the workflow for repeat setup in a second session. The example method includes developing a set of user preferences based on the monitoring and the user input. The example method includes applying one or more machine learning algorithms to develop one or more candidate layouts for selection and application as a hanging protocol.

Certain embodiments provide a tangible computer-readable storage medium including a set of instructions for execution by a processor, the instructions, when executed, to implement a method to determine a hanging protocol for clinical image display. The example method includes monitoring user workflow in a first session. The example method includes accepting user input to record/teach at least a portion of the workflow for repeat setup in a second session. The example method includes developing a set of user preferences based on the monitoring and the user input. The example method includes applying one or more machine learning algorithms to develop one or more candidate layouts for selection and application as a hanging protocol.

Certain embodiments provide a machine learning hanging protocol analysis system. The example system includes an image processing module to process image data to provide one or more features. The example system includes a learning engine to receive processed image data and additional data to learn and adapt a hanging protocol for repeated use by applying one or more machine learning algorithms to the processed image data and additional data. The learning engine is to continue to refine an available selection of candidate layouts based on the processed image data and additional data to provide one or more layout choices for selection to form a hanging protocol for display of image and other data.

Figure 1:
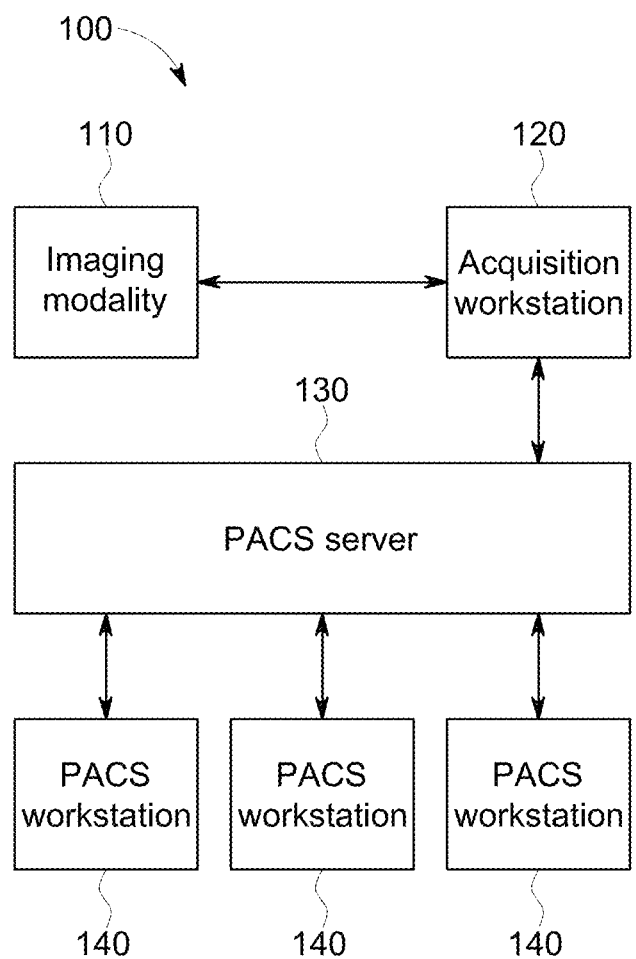
FIG. 1 illustrates an example picture archiving and communication system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain embodiments provide systems and methods for automatic creation of hanging protocols based on information gathered from users. Certain embodiments provide hanging or display protocols that can continue to adapt to a user's needs or wants as image acquisition changes.

Certain examples provide hanging protocols that understand patient anatomy and disease, radiologist tasks and preferences, etc. Certain examples generate hanging protocols while accounting for user preference, data variability and complexity, inconsistent or missing meta data, multiple tasks in one reading, etc.

In certain examples, a log of user interactions is recorded. Related imaging studies are obtained. A mapping is learned from example templates, and that mapping is improved from recorded and analyzed usage data.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, Blu-ray, etc. storing the software and/or firmware.

Hanging/display protocol rules are configured for variable such as modality, body part(s), exam procedure(s), historical count, monitor count, and the like. Accounting for many variables involves many permutations for hanging protocols. Additionally, typical studies now include several series rather than individual images. Instead of examining DICOM header information for a particular image, at least some relationship information for an image series and/or study can be captured and used to determine an appropriate hanging protocol. Using high level characteristics as guidelines for hanging/display protocols can help eliminate explicit rules for all of the individual variables listed above.

FIG. 1 illustrates an exemplary Picture Archiving and Communication System (PACS) 100 used in accordance with an embodiment of the present invention. The PACS system 100 includes an imaging modality 110, an acquisition workstation 120, a PACS server 130, and one or more PACS workstations 140. The system 100 may include any number of imaging modalities 110, acquisition workstations 120, PACS server 130 and PACS workstations 140 and is not in any way limited to the embodiment of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography ("CR") image of a patient's chest. A radiologist or user may then examine the image for any objects of interest, such as tumors, lesions, etc., for example.

The PACS workstations 140 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In an embodiment, the PACS system 100 includes a perspectives manager capable of being used for reviewing images via a plurality of perspectives. The PACS server 130 and/or a PACS workstation 140 may include the perspectives manager, or the perspectives manager may be implemented in a separate system. In an embodiment, each PACS workstation 140 may include a perspectives manager.

In operation, for example, a user, such as a radiologist, selects a set of images, such as screening mammogram images, chest screening images and/or other computed radiography ("CR"), digital radiography ("DR"), and/or digital x-ray ("DX") screening images, to review at a PACS workstation 140. The images may be displayed in a default perspective and/or a customized perspective, for example.

As described above, a user may wish to apply additional processing to one or more images to further enhance features in the image. For example, a user may desire to apply additional processing functions, steps, and/or elements, etc., to an image in order to alter the presentation of an image in conformance with the user's confidence level for making an accurate diagnosis. In other words, different users may desire to apply different or additional processing than that included in a default image processing workflow.

The additional image processing may include any image processing useful to prepare an image for a diagnostic examination. For example, as described above, an image processing step (as a default image processing step or an additional image processing step) can include flipping an image, zooming in an image, panning across an image, and altering one or more of a window, a level, a brightness and a contrast setting of an image. Image data may be displayed on a PACS workstation 140 using the same and/or different processing, display protocol, and/or perspective as other image(s), for example.

PACS workstations 140 may retrieve or receive image data from server 130 for display to one or more users. For example, a PACS workstation 140 may retrieve or receive image data representative of a computed radiography image of a patient's chest. A radiologist may then examine the image as displayed on a display device for any objects of interest such as, for example, tumors, lesions, etc.

PACS workstations 140 are also capable of or configured to retrieve and/or receive one or more hanging protocols from server 130. For example, a default hanging protocol may be communicated to PACS workstation 140 from server 130. A hanging protocol may be communicated between server 130 and a PACS workstation 140 over a wired or wireless connection, for example.

In general, PACS workstations 140 may present images representative of image data retrieved and/or received from server 130. PACS workstations 140 may present the images according to a hanging protocol. As described above, a hanging protocol is a set of display rules for presenting, formatting and otherwise organizing images on a display device of a PACS workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a PACS workstation 140 to display an anterior-posterior ("AP") image adjacent to a lateral image of the same anatomy. In another example, a hanging protocol may direct PACS workstation 140 to display the AP image before displaying the lateral image. In general, a hanging protocol dictates the spatial and/or temporal presentation of a plurality of images at PACS workstation 140.

A hanging protocol may differ from a default display protocol ("DDP"). However, the terms may also be used interchangeably and/or in overlapping circumstances. In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps, functions, blocks, and/or elements, etc., that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a CT or MR imaging device in general or a particular CT or MR imaging device may have a same or similar DDP applied to the image data. In general, a DDP attempts to present image data in a manner most useful to many users.

Conversely, applying a hanging protocol to image data may or may not alter the appearance of an image (based on the image data), but may instead dictate how the image(s) is (are) presented, as described above.

Server 130 may store a plurality of hanging protocols and/or DDPs. The hanging protocols and/or DDPs that are stored at server 130 and have not yet been modified or customized are default hanging protocols/DDPs. A default hanging protocol and/or DDP may be selected from a plurality of default hanging protocols and/or DDPs based on any number of relevant factors such as, for example, a manual selection, a user identity, and/or pre-processing of the image data.

Specifically, a default hanging protocol and/or DDP may be selected based on a manual selection simply by communicating the default protocol once a user has selected that particular protocol. The user may make the selection, for example, at a PACS workstation 140.

In another example, a default protocol may be selected based on a user identity. For example, a user may have a preferred DDP. The DDP may have been customized to meet the user's preferences for a particular temporal and/or spatial layout of images. Once a user gains access to a PACS workstation 140 (for example, by entering a correct login and password combination or some other type of user identification procedure), the preferred DDP may be communicated to the PACS workstation 140, for example.

In another example, a default protocol may be selected based on pre-processing of image data. Pre-processing of image data may include any image processing known to those of ordinary skill in the art that prepares an image for review by a user. Pre-processing may also include, for example, a computer-aided diagnosis ("CAD") of image data. CAD of image data may include a computer (or similar operating unit) automatically analyzing image data for objects of interest. For example, a CAD may include a software application that analyzes image data for nodules in images of lungs, lesions, tumors, etc. However, a CAD application can include any automatic analysis of image data known to those of ordinary skill in the art.

For example, a default hanging protocol that corresponds to CAD findings of lung tumors may provide for the presentation of the posterior-anterior ("PA") and lateral lung images adjacent to each other followed by the presentation of the computed tomography ("CT") lung images, followed by the magnetic resonance ("MR") lung images, for example. In general, a default hanging protocol that corresponds to CAD findings is designed to present images in a spatial and/or temporal layout that is useful to a radiologist. For example, a radiologist may be greatly assisted in his or her review of the CAD findings by viewing the PA and lateral lung images adjacent to each other, followed by previously acquired multi-slice CT and MR images of the lungs.

Therefore, based on CAD findings, a default protocol may be selected from a plurality of default protocols and applied at a workstation 140 in order to present images to a user.

PACS users often wish to run multiple applications on a PACS workstation 140. In addition to a primary PACS workflow or interface application, a user may wish to access other applications such as surgical planning tools, scheduling tools, electronic mail viewers, image processing tools, and/or other tools. For example, PACS users often like to use a PACS workflow engine while viewing electronic mail and accessing information on the Internet. Users of an integrated RIS/PACS system may wish to access both RIS and PACS applications simultaneously. Typically, however, the PACS application occupies all active display area and hides other applications running on the workstation 140. For example, in a PACS workstation 140 having three monitors, the PACS workflow application occupies all three monitors. When an application is initiated, another application may be displaced, or the application may be launched in a sub-optimal display area. For example, a user may launch a data management or diagnostic processing software at a three-monitor PACS workstation 140, and the application may launch on a color monitor, displacing images displayed on the color monitor. Typically, a user would have to manually reorganize applications to display the management application on a grayscale monitor and the images on the higher resolution color monitor.

Certain embodiments provide an adaptable PACS system 100 accommodating a plurality of displays such that each display operates with a separate display window. All display windows are controlled internally by a primary window that is transparent to users. The primary, transparent window tracks which window or windows have the PACS application and which window(s) have other applications and/or data. Thus, the PACS application and other applications may be simultaneously displayed on a plurality of displays.

Certain embodiments provide dynamic configuration of displays associated with PACS workstation 140. The primary window allows interaction or application(s) and data across multiple windows. The PACS workstation 140 operates a transparent, primary window including a plurality of windows across a plurality of displays.

Selection of a hanging/display protocol on a PACS workstation may be based on a plurality of criteria, such as a number of connected displays, a modality, an anatomy, and a procedure, for example. Based on these criteria, a user may create multiple protocols with one default protocol used to display an image study. For example, a hanging protocol may be created for a particular display configuration. A user creates different hanging protocols to properly display a study on different display configurations.

However, certain embodiments allow creation of a protocol including a plurality of perspectives or views, for example. Using one protocol with multiple perspectives/views, a user may associate different perspectives/views for different display configurations with the protocol. For example, a hanging protocol may include multiple perspectives with one default perspective. The default perspective may be used to display a study unless otherwise specified and/or determined manually or automatically, for example.

In certain embodiments, hanging protocols with perspectives/views may use one or more criteria to select a protocol for display. For example, a modality, an anatomy or body part, a procedure, and/or a default view for a display configuration, may be used to select an appropriate display protocol. For example, a display protocol includes a perspective/view with multiple options depending upon monitor configuration. A user may create a hanging protocol with different view for different display configurations, for example. A user does not have to create different hanging protocols for different monitor configurations but may instead create additional views with the existing hanging protocol. In certain embodiments, a user may switch between different perspectives/views after opening a study.

In certain embodiments, perspectives are views or layouts indicating visual component positioning and interactions between images and/or applications based on workflow, for example. Medical perspectives may be used to create a plurality of benefits. For example, perspectives may provide patient context sharing between different image(s) and/or application(s) that a user views. Additionally, for example, perspectives provide an ability to easily switch between different configurations or perspectives based on which images and/or applications a user wishes to view at any given point. Furthermore, for example, perspectives provide an ability to store or "remember" specific workflow steps. Perspectives provide a mechanism to save and display information relevant to a particular user, group, and/or function, for example. Perspectives may be used to display images and other data for a particular resolution, display type, and/or other configuration, for example.

Perspectives may be used to logically group different images and/or other data or applications. For example, perspectives may be defined for images, examination results, laboratory data, patient history data, structured report data, DICOM data, and/or other data or applications, for example. Rules, configuration options, and/or other criteria may be defined in order to define perspectives. In certain embodiments, perspectives do not eliminate or change information but rather order information in a certain way. For example, information important to a user may be displayed first, with additional information available via different perspectives. In certain embodiments, perspectives may be created automatically based on user selection or other configuration information, for example. In certain embodiments, a perspective may work together with a rules-based context manager to filter and display information.

Additionally, a display protocol, such as a Default Display Protocol ("DDP"), may be adjusted for one or more displays based on content and/or a number of connected display(s). For example, if the PACS workstation 140 is reconfigured from a three monitor configuration to a one monitor configuration, the DDP may be modified accordingly. Certain embodiments adapt a DDP based on application(s) closed and/or opened as well as window(s) activated and/or deactivated. For example, a DDP may determine what information is displayed to a user. A DDP may adapt based on a number of available monitors and a number of images to be displayed, for example (e.g., four images are shown on one available display; eight images are shown on two available displays, etc). PACS workstation 140 may configure a DDP for any multi-monitor full screen and/or partial screen applications. Additionally, one or more applications may be resized on a single screen (e.g., minimize, maximize, and/or resize).

Healthcare information systems, such as a Hospital Information System (HIS), Radiology Information System (RIS), Cardio-Vascular Information System (CVIS) and/or Picture Archiving and Communication System (PACS), are the critical infrastructure for efficient patient care. The PACS system may store images from different modalities, such as Computed Tomography (CT), Magnetic Resonance (MR), etc., while a RIS, CIS or HIS may contain non-image information, such as physician reports, disease history, and/or other patient associated data. In order to make a conclusion regarding a reviewed case, a clinician organizes relevant data in a certain order on a set of monitors, for example. This order may depend on a plurality of parameters, such as an imaging modality of the exam under review, existence of historical images and number of historical images, previous reports, list of prescribed medications, etc.

Figure 2:
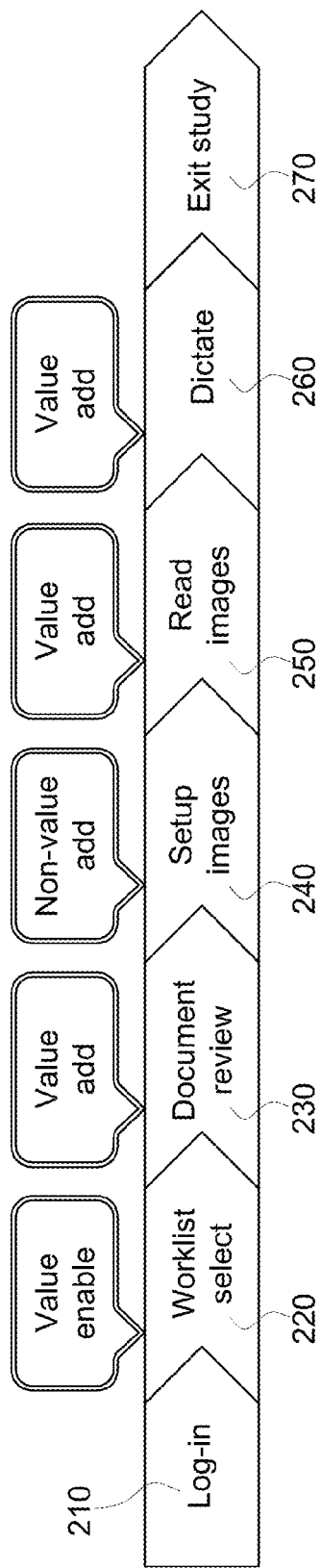
FIG. 2 illustrates an example radiology workflow.

FIG. 2 illustrates an example radiology workflow. A radiologist logs into a system, such as a PACS (block 210), reviews his/her worklist (block 220), and selects a study to review (block 230). A PACS system may provide predefined and/or user configurable Hanging Protocols (HP), for example. In PACS systems, the HP is to open imaging data in an initial setup (block 240) that is optimal or otherwise desirable for a reviewing physician, depending on a type of case he/she is reviewing (block 250). During or after image reading (250), the user can dictate regarding findings, notes, instructions, etc. (block 260), and then exit the study (block 270).

However, a number of parameters and variability of parameters in input data can be so great that, in some cases, manual pre-configurations of HP completely fail. Furthermore, the existing tools for HP configurations are very complex. Typically, the actual configuration is done by product specialists, support engineers or information technology (IT) administrators based on guidance from physicians. The complexity of the HP configuration tools and the dependence on experts to operate them does not allow users to apply modifications or improvements on their own.

Different methods have been proposed to automatically create HPs. In U.S. Patent Application Publication Number 20100080427, entitled "Systems and Methods for Machine Learning Based Hanging Protocols," and assigned to the assignee of the present application, one or more high level characteristics are captured for an image study based on relationship of the images in the study. An image is classified based on the low level characteristics of the images. Combining low and high level characteristics, the machine learning engine classifies the study and determines an appropriate hanging protocol, based on this classification. In U.S. Patent Application Publication Number 20080166070, entitled "Method for Providing Adaptive Hanging Protocols for Image Reading", and assigned to the assignee of the present application, a productivity factor of each HP is monitored and calculated based on efficiency of the user during a reading of the study. The system may then, advise the user to switch to another hanging protocol, defined by another user, if its efficiency factor is larger.

System and methods in U.S. Pat. No. 7,525,554, entitled "Content Based Hanging Protocols Facilitated by Rules Based System", and assigned to the same assignee as the present application, a user is allowed to edit a default hanging protocol, create and apply additional display rules, and track a number of times the user selects different display rules for different image modalities. Then, based on one or more thresholds, the system automatically decides whether the default hanging protocol should be modified, and, after user confirmation, applies the changes.

At present, there is no solution that allows a user to directly and explicitly 'teach' a system how to set up a HP. Furthermore, in some clinical workflow cases, a physician review process is divided into several well defined and specific steps. For example, in a certain workflow, the radiologist might always start by reviewing the x-ray images and then proceed to the CT scans. In another workflow, the radiologist might decide to first review the current study and only later bring up prior studies for comparisons. These well-defined step-by-step workflows may change from user to use and site to site, but are very fixed and predictable for a certain user or users and a given workflow. No prior system allows users to explicitly 'teach' elements or components of a workflow (e.g., what data and in which manner should be set up at the beginning of each element, step, etc.). Certain examples provide such a teaching or learning workflow.

Figure 3:
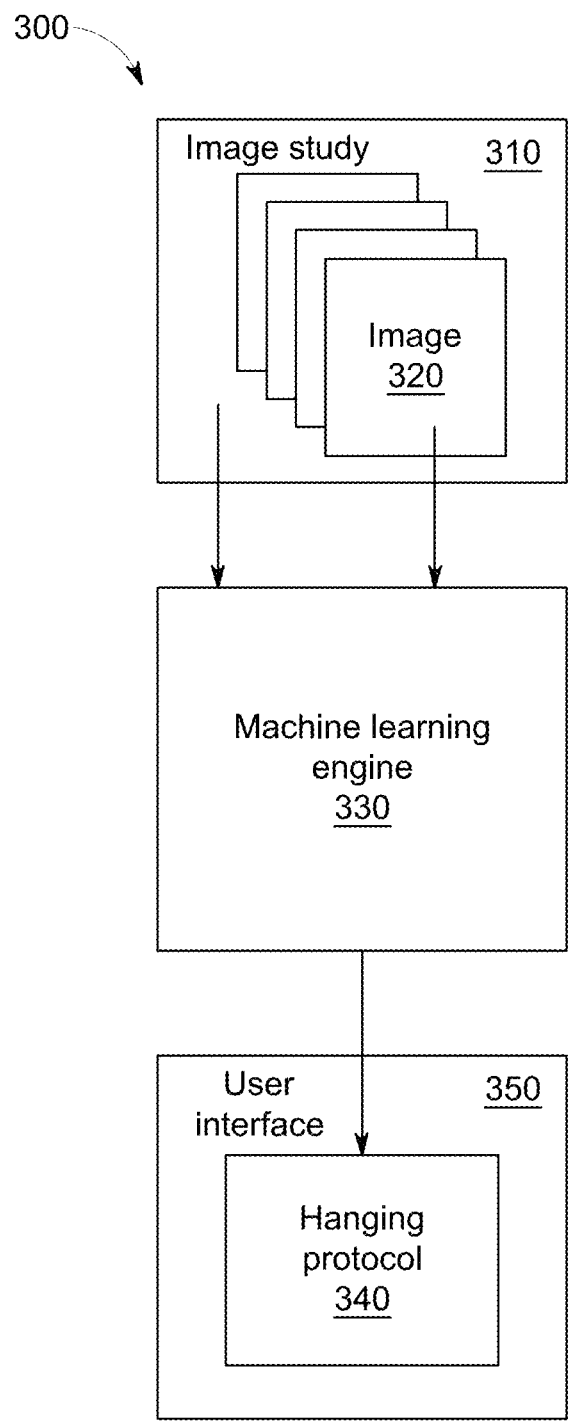
FIG. 3 depicts an example of a system for determination of an appropriate hanging or display protocol in accordance with an embodiment of the present invention.

FIG. 3 depicts an example of a system 300 for determination of an appropriate hanging or display protocol. The example system 300 includes an image study 310 including study information, one or more individual images 320 including image DICOM header information, a machine learning engine 330, a hanging or display protocol 340, and a user interface 350. The components of the system 300 can be implemented in software, hardware, and/or firmware, for example.

In operation, the study 310 information and individual image 320 information are extracted from an image study and provided or otherwise made accessible to the machine learning engine 330. Based on initial user input and stored information gathered from past layouts, the engine 330 generates/selects a hanging/display protocol 340 for displaying images and/or other data via the user interface 350. For example, an artificial neural network and/or other adaptive processing model can be used by the machine learning engine 330 to select an appropriate hanging protocol 340 based on available image header information, inter-image study information, and saved prior information.

In certain embodiments, a type of machine learning technique used is an artificial neural network. Hanging/display protocol algorithms can use DICOM header elements to determine high level characteristics for a study. Then, initially, a user lays out one or more image/series. Correlations between the high level characteristics and the user layout are stored in nodes of the artificial neural network. As the user makes changes to the layout over time, the artificial neural network nodes are updated, and the nodes continue to evolve. When the user displays a new study, the algorithms determine the high level characteristics of the study and classify them according to different layouts. In certain embodiments, artificial neural networks are used in systems wherein an algorithmic solution cannot be formulated; many examples of desired behavior can be obtained; and/or structure is selected from existing data, for example. Although artificial neural networks are discussed above, other forms of artificial intelligence, such as fuzzy logic, Boltzmann machine, Bayesian network, etc., can be used as machine learning techniques to determine an applicable hanging or display protocol.

For example, the engine 330 can account for one or more high level study characteristics including detection method used, number of relevant images for the detection method, and image resolution compared to monitor resolution based on relationships between image DICOM header elements. Based on a patient's different series in current and previous studies, for example, a hanging protocol algorithm used by the engine 330 can determine a methodology used to detect abnormalities. That methodology can help rank or select a hanging protocol for use in display of image(s) and/or other information on a user display. Different methodologies may involve different image layouts and thus different hanging protocols or DDPs, for example.

For example, if a patient has current and prior CT images, display priority and position may be given to the current and most recent prior image(s) as space and display quality allow. As another example, if images for a patient were obtained with and without contrast injection, a current study's pre and post contrast images may be displayed next to each other while previously study's pre and post contrast image series are displayed next to each other. Extra contextual information gathered from examining relationships between different series of images provides improved accuracy in modeling and display of a study.

Certain examples provide a "smart" workflow feature to improve a radiologist workflow. Rather than manual pre-configurations of layouts and a large number of parameters, example systems and methods learns users' preferences as they work so that when they open a new study/exam, data is set up in a way that is preferred by the user (e.g., with respect to layout, viewports, automatic post-processing, etc.). For example, the "smart workflow" feature relies on a machine learning algorithm that tracks a way a user or a group of users create image setups in particular workflows and reproduces these layouts for new studies of this type, overcoming variability in the data. Thus, even if the algorithm makes mistakes and does not produce optimal image setups initially, the algorithm accepts corrections from the user, adapts, and converges to the 'optimal' image setups after the users 'teaches' it, possibly a few times.

Certain examples speed up and/or increase efficiency in a user's workflow according to user preferences.

Certain examples provide a "smart" HP to automatically overcome different labeling of a same study type (e.g., outcome of modalities from different vendors, different technicians, etc.). For example, a user 'teaches' one or more machine learning algorithms to take into account certain combination(s) of other parameters.

Certain examples provide a "smart" HP to automatically overcome a different sequence order in a study. In certain prior solutions, with no further input from a system or user, a HP simply hangs an image series based on an order or images in the series, in the hope that a technician operating the modality created the series in a predictable and deterministic order. However, this logic breaks down as soon as modalities from different vendors are used or technicians are replaced. In certain examples of the presently disclosed technology, users "teach" a machine learning engine, through simple interaction, which parameters actually control logic relating to which images of an image series are to be initially displayed on which viewport in a viewing application or display.

Certain examples provide advanced automatic loading of relevant priors. For example, a "smart workflow" system learns from a user regarding hanging of historical study(-ies) along with a current study (e.g., of the same patient). For example, in Oncology, users track lesion growth over time and, therefore, wish to hang prior and current images for review together.

In certain examples, a user can teach a "smart workflow" system to automatically load relevant priors, but not of same patient, as a "teaching file" and/or for comparison with a previously diagnosed case, for example.

In certain examples, a machine learning engine of a "smart workflow" identifies keywords in documentation such as exam order, procedure codes, prior reports, etc., and, if keyword(s) are found in the documentation, uses the keyword(s) as parameters for learning.

In certain examples, a "smart workflow" learns and applies appropriate computer vision tools to reproduce clinically accurate window leveling, zoom, pan, rotation, and/or other manipulation(s) of images.

In certain examples, a machine learning engine learns to appropriately set up or position documentation that is relevant to displayed imaging data, including auto-rotation of scanned documentation so that the documents "hang" or are displayed correctly for immediate reading, for example.

In certain examples, once a user opens an imaging exam, a HP system automatically "hangs" or positions various images and data from the imaging dataset(s) on one or more monitors that are being used on a designated workstation for review of the imaging exam. If the setup is in accordance with the user's preference, then the user can proceed with the review with no further delay. However, in the case where the user is not pleased with the initial hanging and needs or wants to further interact with the data before the actual case review begins, then the user may further refine (e.g., use a "learn this setup" button) the HP before proceeding with the review, so that the system may learn by example from his/her preferred setup, for example. Once the "learn this setup" is used, the system creates a snapshot of the setup and associated parameter(s). In certain examples, parameter(s) captured by the system include one or more of:

1. User (e.g., physician) identifier
2. Time stamp
3. Unique identifiers (IDs) of a study along with prior studies that are associated by database relationship with a current study
4. Study body part
5. Number of monitors being used
6. Layout of viewports on the monitors
7. Rendering parameters such as show/not show overlays, image group rules, etc.
8. For each viewport in the layout
   a. Viewport location in the layout
   b. Viewport size
   c. Single slice or stack viewing mode
   d. Study identifier
   e. Historic level
   f. Series identifier
   g. Window-level
   h. Which image(s) in series are rendered in setup
   i. Zoom
   j. Pan
   k. Rotation
   l. Measurement (if applied)
9. Information on linked viewports
10. Screen capture (of all monitors)
11. Keywords for understanding of the case, extracted from the following:
    a. Procedure name
    b. Keywords from exam order
    c. Prior reports (if exist)

In certain examples, a user wishes to teach the system additional workflow steps, beyond just the initial hanging. Then, the user may set up the imaging data in a preferred way and select "learn this workflow step" (e.g., via a button press, item selection, mouse click, etc.).

Each time the user chooses to teach the system, a current step's number is displayed via a graphical user interface, and the interface allows the user to edit a current or entire set of workflow step snapshots, for example. The user may go back to a certain step or element of a workflow or interface configuration, obtain an immediate setup of that element and be allowed to re-name and or modify the element, for example.

Figure 4:
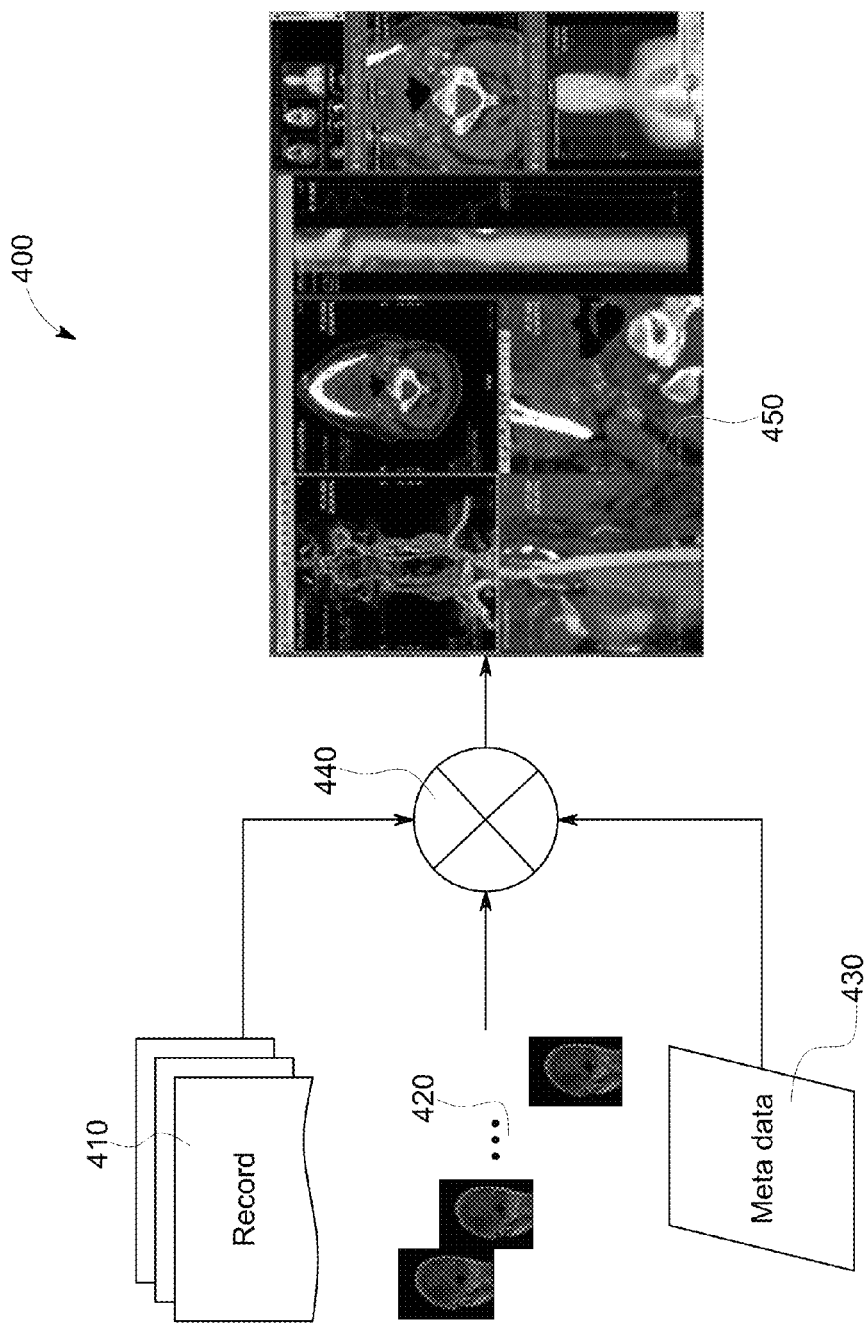
FIG. 4 provides an example visualization of a mapping obtained through machine learning.

In certain examples, a machine learning module involves a training set of examples of hanging protocols of previous exams. As described above, these exams can have metadata associated with them, including user and site information. The examples are characterized by features that have been deemed relevant to hanging protocols, for example. The features can be computed based on numerical variables (e.g., number of monitors, etc.), categorical variables (e.g., body part, etc.) and/or free-form text (e.g., series description, etc.). An output of the learning engine is a "hanging protocol" that is characterized by parameters that allow the system to generate the final layouts. FIG. 4 provides an example visualization of a mapping obtained through machine learning.

As shown in the example mapping 400 of FIG. 4, one or more reports 410, one or more images 420 (e.g., image(s) associated with the report(s), etc.), and/or one or more meta-data 430 (e.g., meta data associated with image(s) and/or report(s), etc.) are combined or mapped via a mapper 440 to generate a layout 450. The layout 450 provides a visualization of the mapping between image(s), report(s), and metadata, for example.

Figure 5:
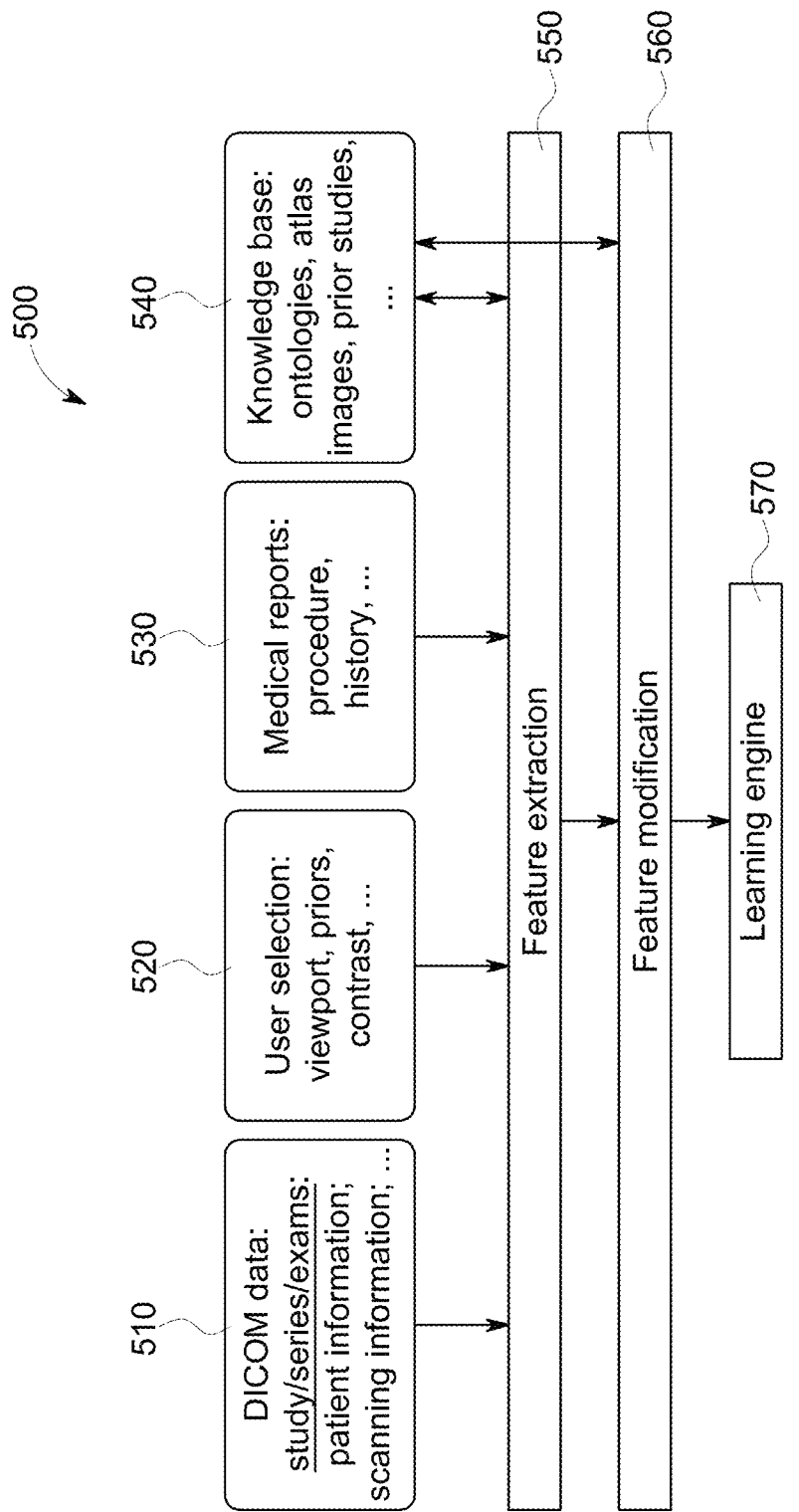
FIG. 5 depicts a high level data flow for an example machine learning algorithm.

FIG. 5 depicts a high level data flow for an example machine learning algorithm. As shown in the example data flow 500 of FIG. 5, a learning engine 570 is provided with a variety of information in the form of features from which to learn preference(s), priority(-ies), requirement(s), etc., for one or more hanging protocols and/or one or more user(s). Information, such as DICOM data 510, user selection 520, medical report(s) 530, knowledge base 540, etc., is provided for feature extraction 550. DICOM data 510 can include patient information, scanning information, etc., for one or more studies, image series, patient exams, etc. User selection 520 can include viewport(s) information, prior(s) displayed, contrast selected, etc. Medical reports 530 can include procedure, history, etc. The knowledge base 540 can include information such as ontologies, atlas images, prior studies, related studies, best practices, etc.

Following feature extraction 550 from the provided information 510-540, extracted features are provided for feature modification 560. For example, one or more algorithms can be applied to the extracted features to enable the learning engine 570 to process the features and develop a hanging protocol recommendation.

In certain embodiments, the learning engine uses "lazy learners" algorithms with respect to hanging protocol(s). In artificial intelligence, lazy learning is a learning method in which generalization beyond the training data is delayed until a query is made to the system, as opposed to in eager learning, where the system tries to generalize the training data before receiving queries. Employing a lazy learning method, such as case based reasoning, provides an approximately local target function, such as in the k-nearest neighbor algorithm. Because the target function is approximated locally for each query to the system, lazy learning systems can simultaneously solve multiple problems and deal successfully with changes in the problem domain, for example.

Lazy learners are parameter-free learning algorithms, in which learning is delayed until a test case or query is posed to the system. Lazy learners are useful, for example, when the output is high-dimensional, since the target output is approximated locally. Case-Based Learning is a well-suited candidate for lazy learning and works as follows. Given a training set of $(X_1, H_1), (X_2, H_2) \ldots (X_n, H_n)$, where $X_i$ is a vector of features of an i-th exam and $H_i$ represents parameter(s) of a handing protocol, a query point $X_q$, $H_q$ is approximated as follows. First, k-nearest number(s) of $X_q$ from the training set are calculated. A number of neighbors calculated is a design parameter. A distance between two cases is also a design parameter, and various metrics such as $L_1$-norm, Mahalanobis, Scaled Euclidean, etc., can be used.

For example, a Mahalanobis distance of a multivariate vector $\chi = (\chi_1, \chi_2, \chi_3, \ldots, \chi_N)^T$ from a group of values with mean $\mu = (\mu_1, \mu_2, \mu_3, \ldots, \mu_N)^T$ and covariance matrix S is defined as:

$$D_M(\chi) = \sqrt{(\chi-\mu)^T S^{-1} (\chi-\mu)}.$$

A Euclidean distance, for example, may be defined as follows. If $p = (p_1, p_2, \ldots, p_n)$ and $q = (q_1, q_2, \ldots, q_n)$ are two points in n-dimensional space, then the Euclidean distance from p to q, or from q to p is given by:

$$d(p, q) = d(q, p)$$
$$= \sqrt{(q_1 - p_1)^2 + (q_2 - p_2)^2 + \ldots + (q_n - p_n)^2}$$
$$= \sqrt{\sum_{i=1}^{n} (q_i - p_i)^2}.$$

An L1 norm may be defined as follows. If $p=(p_1, p_2, \ldots, p_n)$ and $q=(q_1, q_2, \ldots, q_n)$ are two points in n-dimensional space, then a $L_1$ norm distance between from p to q, or from q to p is given by:

$$d_1(p, q) = \|p - q\|_1 = \sum_{i=1}^{n} |p_i - q_i|,$$

Once k nearest neighbors are found, final output parameters are generated by adapting by the solutions of the neighbors. A distance metric, weighting functions for various features, number of nearest neighbors considered and functions for solution adapting are chosen either by trial and error or automatically learned so as to optimize or improve performance of the case-based reasoning (CBR) system using statistical techniques such as cross-validation, for example.

In certain example, users can provide feedback regarding a generated hanging protocol using a visual interface. For example, the feedback is used to adjust weight(s) used for different features to calculate a similarity metric using one or more evolutionary algorithms to reduce or minimize an error in performance of the learning algorithm. Principles of an evolutionary algorithm (EA) define a general paradigm that is based on a simulation of natural evolution, for example. EAs perform searches by maintaining at any time t a population $P(t)=\{P_1(t), P_2(t), \ldots, P_p(t)\}$ of individuals. "Genetic" operators that model simplified rules of biological evolution are applied to create a new and more superior population P(t+l). This process continues until a sufficiently good population is achieved, or some other termination condition is satisfied. "Sufficiently" can be defined according to one or more user and/or system specified constraints, for example. Each $P_i(t) \in P(t)$ represents, via an internal data structure, a potential solution to an original problem. Closely linked to the representation of solutions is a fitness function y: P(t)–*R, that assigns credit to candidate solutions. Individuals in a population are assigned fitness values according to some evaluation criterion(-ia). Highly fit individuals are more likely to create offspring by recombination or mutation operations, whereas weak individuals are less likely to be picked for reproduction and eventually die out. A mutation operator introduces genetic variations in a population by randomly modifying some of the building blocks of individuals.

Evolutionary algorithms are essentially parallel by design, and at each evolutionary step a breadth search of increasingly optimal sub-regions of the search space is performed. Evolutionary search is a powerful technique of solving problems and is applicable to a wide variety of practical problems that are nearly intractable with other conventional optimization techniques. Though practical evolutionary search schemes do not guarantee convergence to a global optimum in a predetermined finite time, they are often capable of finding very good and consistent approximate solutions.

In certain examples, a learning engine uses eager learning algorithms such as neural nets or support vector machines where the system learns a general, input independent target function during training of the system. For eager learning, one of several approaches can be selected for use. In a first approach, target functions can be trained to map an input feature vector to a set of hanging protocols. The easy learners, therefore, implement a classification algorithm that maps the input vector to a categorical label that determines the hanging protocol(s) to be used. Another approach is to train learners to regress for each individual parameter of a final hanging protocol.

In certain examples, features based on free-text fields are analyzed using text-mining algorithms. Open-source text mining software, such as Apache Lucene®, is used to remove stop words, stem words to base form, and identify relevant concepts (e.g., imaging modalities, body parts, etc.). In certain examples, machine learning algorithm(s) are integrated with ontologies such as Foundational Model of Anatomy, Neuronames, Brinlex, etc. These ontologies are augmented with smart hanging protocol (SHP)-related information including imaging properties, abbreviations of body parts, etc. The ontologies allow the machine-learning algorithms to compute similarity metrics between two free-form text strings, for example.

Figure 6:
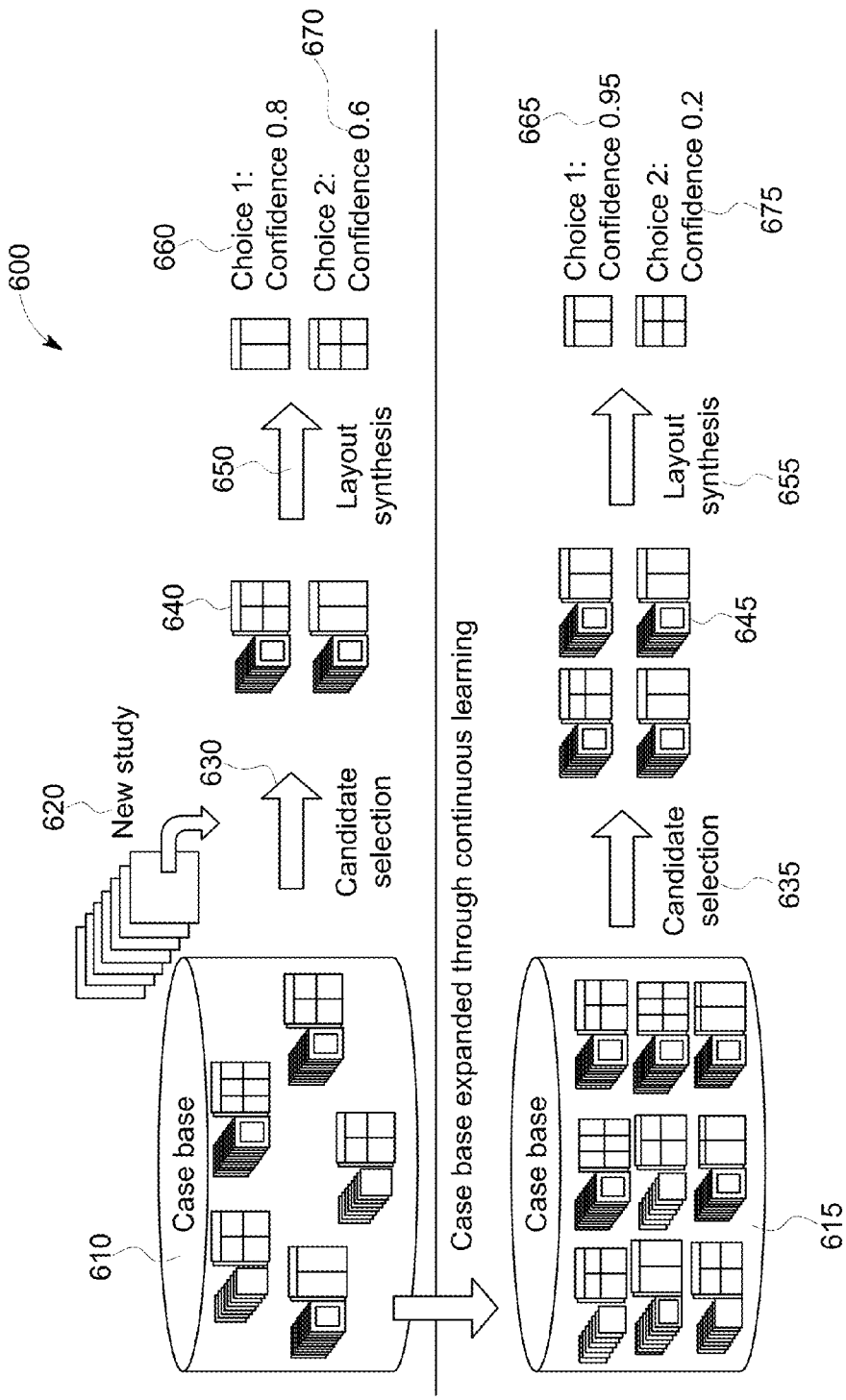
FIG. 6 depicts a flow diagram of an example case-based reasoning system.

FIG. 6 depicts a flow diagram of an example case-based reasoning system. The example system 600 includes a case base 610 of one or more learned (e.g., captured, observed, taught, etc.) hanging protocol layouts/configurations. For a new study 620, candidate selection 630 provides one or more layout candidates 640 for layout synthesis 650 according to one or more algorithms, guidelines, rules, preferences, etc. Layout synthesis 650 provides one or more choices 660, 670 for automatic and/or user selection to apply to display images, reports, tools, etc., on a user display. For example, in FIG. 6, candidate selection 630 and layout synthesis 650 provide a two layouts: choice 1 with an associated confidence score of 0.8 and choice 2 with an associated confidence score of 0.6. The user and/or a program can select one of the layout choices 660, 670 to be applied as a hanging protocol to a user display.

As illustrated in the example of FIG. 6, an available case base 615 can continue to expand due to continuous learning and monitoring of display layout activity, user feedback, etc., to provide more and/or better candidates for selection. A subsequent candidate selection 635 provides additional layout candidates 645 for layout synthesis 655. In the example of FIG. 6, layout synthesis 655 provides two choices 665, 675: choice 1 with an associated confidence value of 0.95 and choice 2 with an associated confidence value computed to be 0.2.

In certain examples, the system also applies image processing as part of the learning mechanism. For example, in a case where a user reviews scanned documentation, the system automatically centers and rotates the document so as to avoid additional manipulation and setup time. For each workflow, relevant documents used for review are learned. A default preference and a user-specific preference list are learned for each review and are used in later reviews.

In certain examples, at a certain point of an image reading workflow, when a user wishes to review an image series such as CT or MR, the user requests or desires a certain view of the image series. The view may include information such as view position, orientation, contrast, etc., for a review. For example, a user may like an initial rendered image to be at a "start position" of a region of interest (ROI). For example, for an MR brain image, it is efficient to have a hanging protocol open the series at a frame where the brain starts, which occupies valuable seconds. This is even more significant in an example of a full body CT scan, when, based on the exam order or prior reports, a radiologist needs or wants, at some point in the workflow, to begin a review of a certain organ, such as the liver. While the radiologist is able to scroll through the series and find any organ, the manual process takes valuable time. In certain examples, the user "teaches" the system by scrolling to an organ in question and then choosing a "learn this" button, icon, tab, etc. A learning module combines machine learning algorithm(s) with image processing algorithm(s). For example, in a liver lesion case, if the user taught the system to start or jump to a review of the liver at some point in the workflow, then the system reacts accordingly.

In certain examples, the user may wish to "teach" the system to load images with certain post-processing applied to them, such as automatic measurements, annotation, comparisons with previous studies, etc. Thus, if a user first applies a measurement and then selects "learn this", under the same conditions, the system attempts to automatically apply the measurement and save the interaction time.

Figure 7:
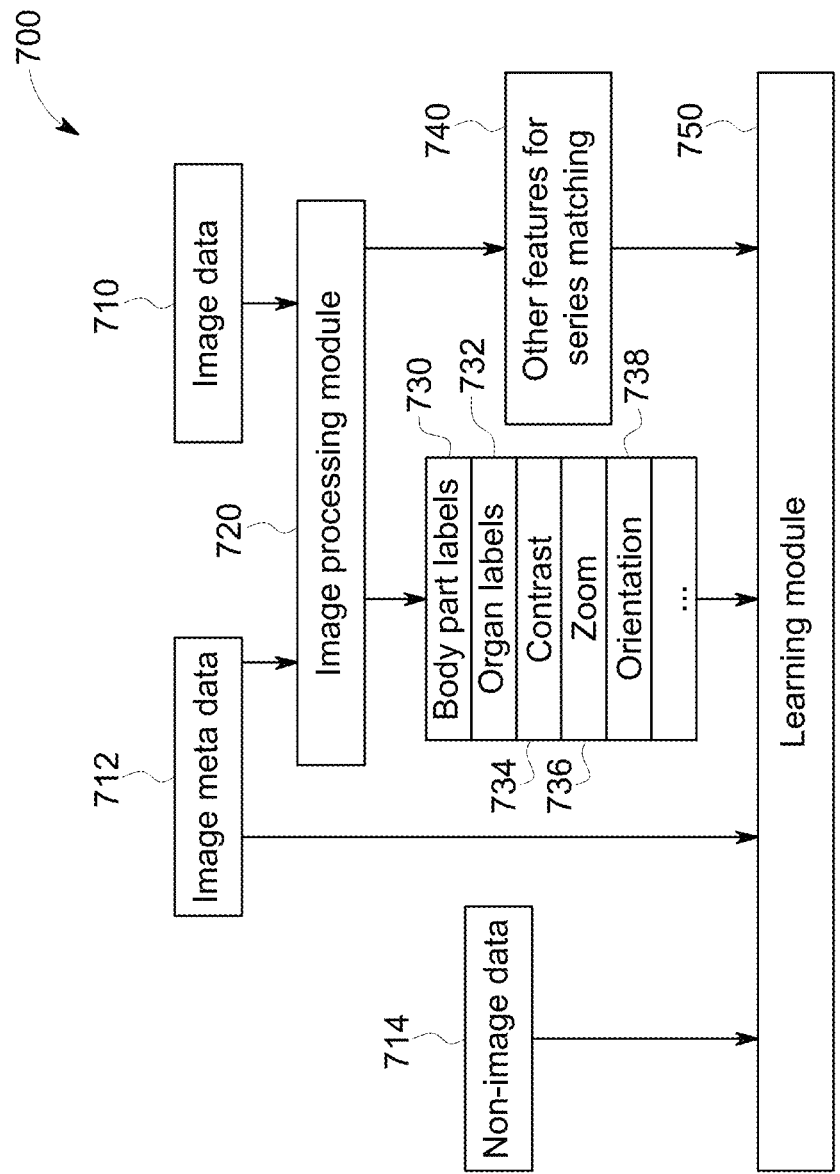
FIG. 7 illustrates an example hanging protocol learning system including an image processing module.

FIG. 7 illustrates an example hanging protocol learning system 700 including an image processing module 720. In the hanging protocol learning system 700, image data 710, image meta data 712, and non-image data 714 can be provided to a learning module 750. In the example image processing module 720, images 710 are pre-labeled with image content description using image analysis algorithm(s). The labels include information such as an occupying body region 730, organ type 732, contrast 734, zoom 736, orientation used 738, etc. Other features 740 can be used for series matching as well or instead. The learning module 750 uses labels in the images and associated information, such as patient history, exam procedure, etc., to learn user preference(s). When the user opens a new study, the smart workflow automatically displays image region(s) of interest in preferred monitor, viewport, orientation, and/or contrast, etc.

In certain examples, scanned body part(s) are labeled using image processing algorithm(s) based on both image and ontology information. Each image slice is given a label that identifies to which body part the image belongs. Identification and labeling can be performed using machine learning based approaches, histogram based approaches, methods based on image features, and so on. On a lower level, individual organs in the images are labeled manually, semi-automatically, or automatically using image processing algorithm(s). The organs can be labeled by location(s), bounding box(es), pose(s) that include locations, orientations, and sizes. The organ shapes can be represented using simple models (e.g., rectangles, ellipsoids, circles, etc.) or sophisticated models (e.g., a statistical atlas, etc.). Organ labeling can also be performed by assigning labels to image locations through manual, semi-automatic, or automatic segmentation. The organ labels help enable quick and accurate initial display and navigation of the images, as well as assist auto zoom and contrast adjustment on the focused organs for better visualization, for example.

When displaying a new study, the smart workflow compares each image series to the learned examples and determines which series is displayed on every viewport. The image series are compared based on imaging modalities, imaging protocols, parameters, image features including orientation, size, intensity profile, etc. These features are obtained or derived from image metadata, from image processing, and/or from abstraction of imaging information, for example. The image series can also be compared through image registration, for example.

In certain examples, the workflow learns preferred image slices or planes that the user wants to view and automatically determines the slices or planes to be displayed when loading a new study based on image labels.

In certain examples, when comparing to historical data for the same patient or a different patient with similar pathology, the workflow can automatically display the images at same body locations from different studies based on image registration and/or labeling.

Thus, in certain examples, users set up data in a manner preferred by the users and teach a learning system in real-time (or substantially real-time). Furthermore, certain examples provide a system designed with a goal of fast convergence to what users perceive as optimal "hanging" and overcome variability in input data and user preference. Certain examples increase a user's productivity and allow users to focus on the diagnostic aspects of the review, thereby improving healthcare quality. Certain examples provide methods and systems to teach, guide, and/or facilitate an entire workflow. Certain examples provide a user interface allowing a user to provide input including an image system, and the image review system learns from the user input.

FIGS. 8-12 provide example hanging or display protocol layouts and application of a learning algorithm for hanging protocol configuration and application.

Figure 8:
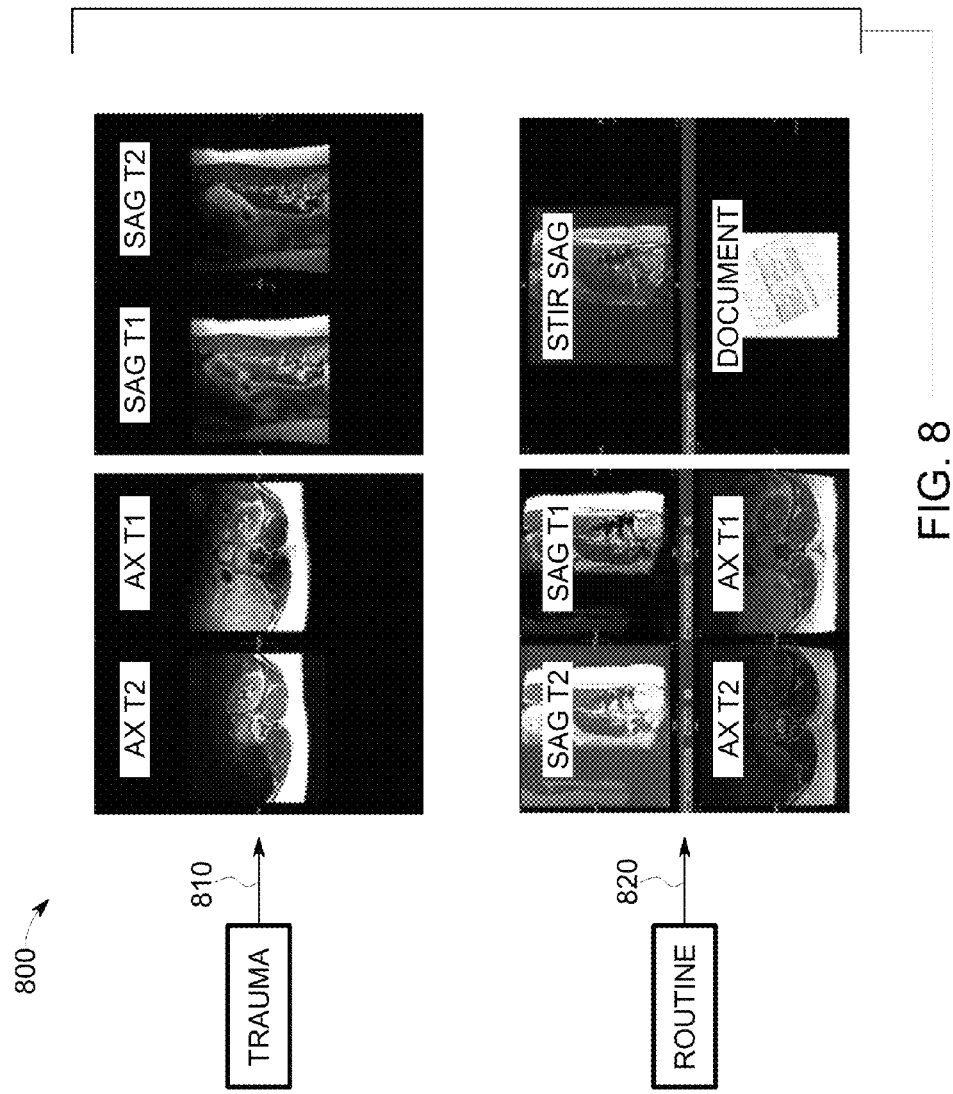
FIGS. 8-12 provide example hanging or display protocol layouts and application of a learning algorithm for hanging protocol configuration and application.

FIG. 8 illustrates example display protocols 800 for a trauma case 810 which is positioned ahead of a routine case 820 for radiologist review. As shown in the example of FIG. 8, a user may want a different layout for each different type of case to be reviewed, depending upon priority, circumstances, time constraints, what they are looking for, etc. In this example, for the trauma case 810, the user wants to display two horizontal axial (AX) images T1 and T2 in the left viewport or display and two sagittal (SAG) images T1 and T2 in the right viewport/display. However, for the routine case 820, the user would like a four panel view of two sagittal images T2 and T1 in an upper portion of the first view and two axial images T2 and T1 in a lower portion of the first view along with one vertical sagittal image STIR in an upper portion of a second view along with a scanned document in a lower portion of the second view. If the user modifies the arrangement, a learning or configuration option (e.g., menu item, button, etc.) can be provided for the user to instruct the machine to remember this configuration (e.g., continue the machine's learning process based on user, type, layout, etc.).

Figure 9:
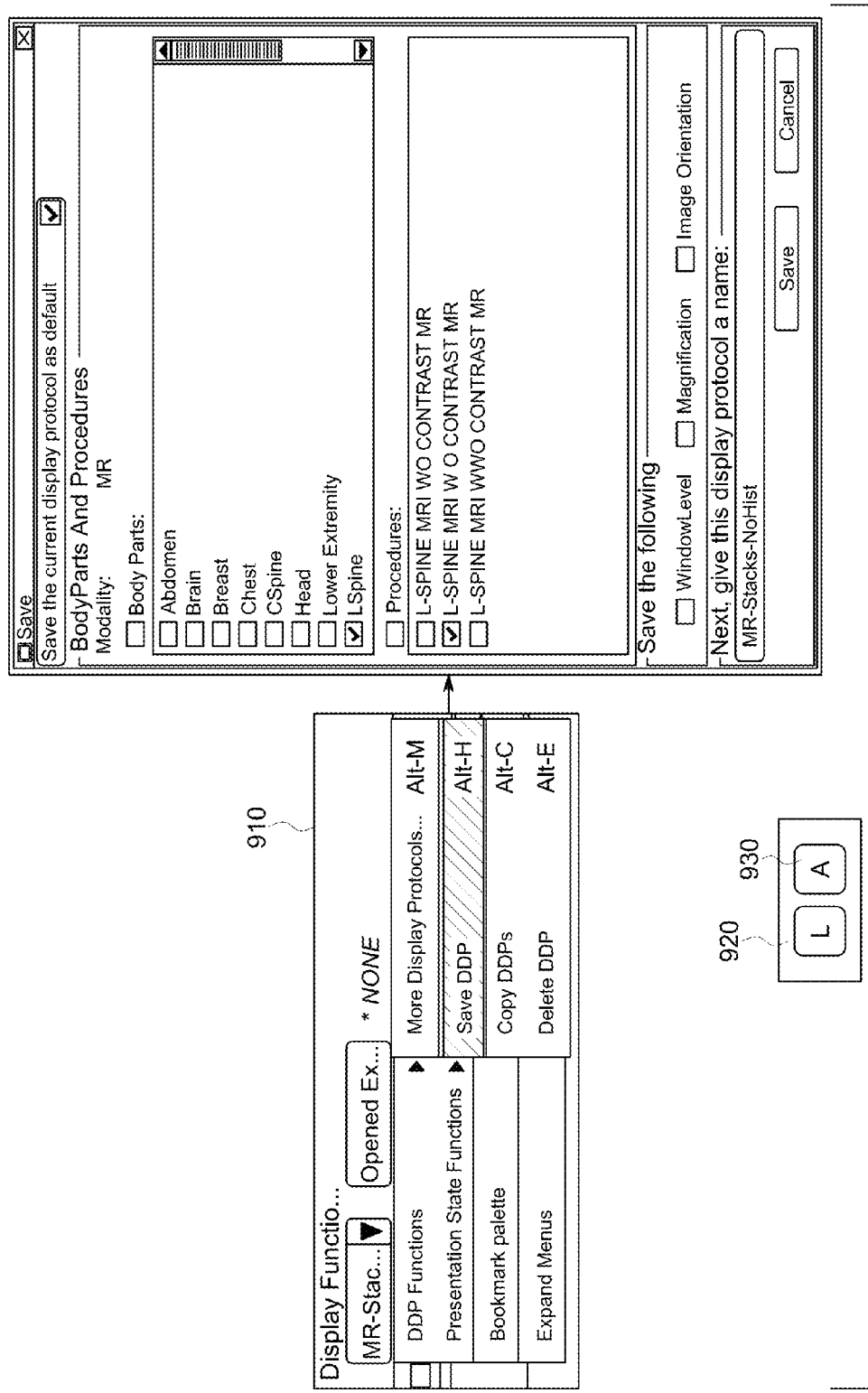

For example, as shown in FIG. 9, rather than requiring a user to navigate a cumbersome menu 910 to save a default display protocol, certain examples provide a simplified interface including a learning button 920 and apply button 930.

Thus, in certain examples, a viewer or user interface can include a user-selectable option (e.g., a "learn" button) to trigger the system to capture, record, and/or otherwise remember a particular layout and/or portion of a layout for a hanging protocol.

Figure 10:
Figure 11:
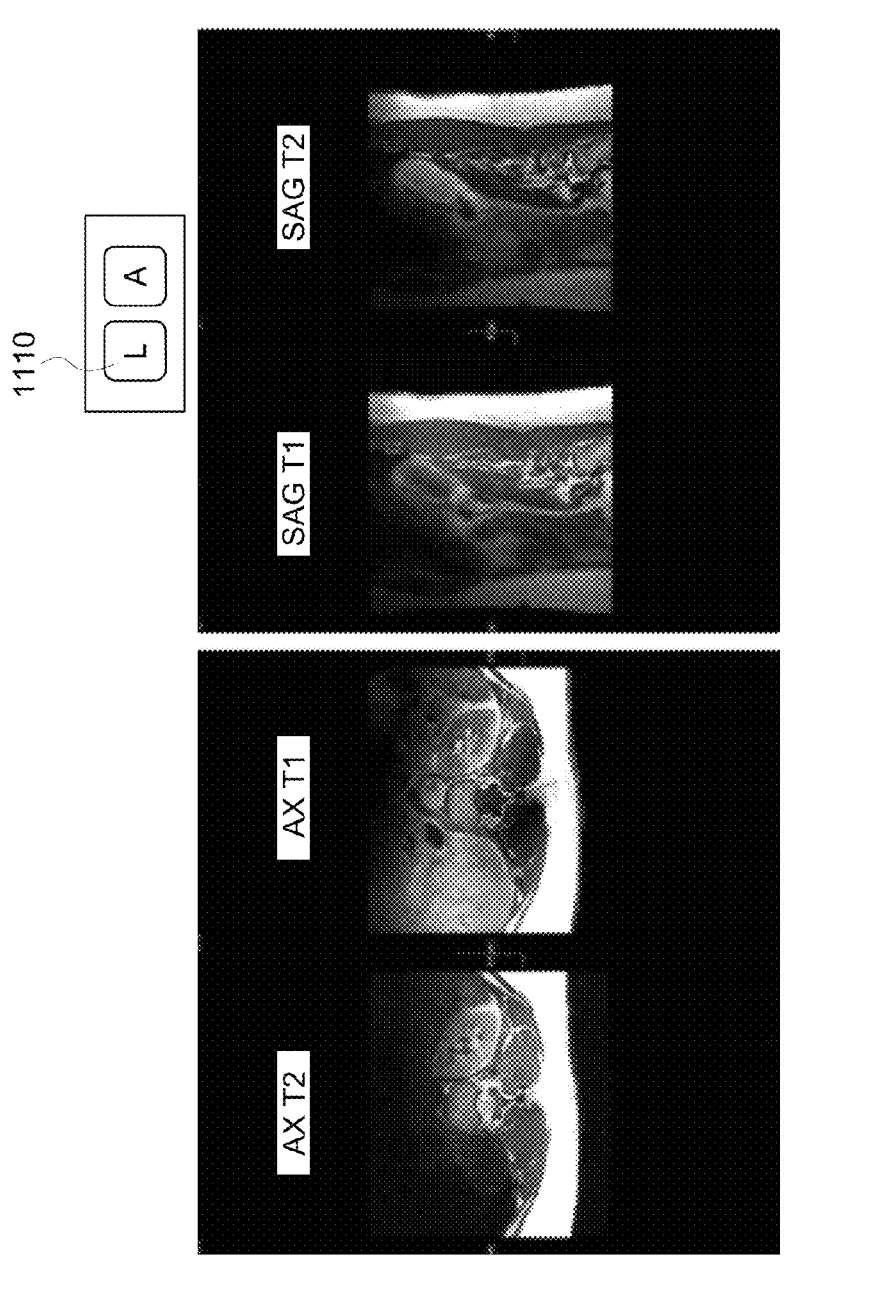

FIGS. 10 and 11 provide example views of desired display protocols for routine and trauma cases, respectively. The system can provide a default display protocol based on what it has learned, which can be confirmed by the user and/or modified by the user, for example. If the user wishes for the system to modify or expand its hanging protocol behavior based on a user modification of the hanging or display protocol, the user can select the learn button 1010, 1110 to add this modification and/or layout configuration to the system's universe of hanging protocol options for candidate selection and processing based on one or more criterion including user, role, case type, urgency, available exam data, etc. Rather than having to navigate multiple menus with multiple options to save a display protocol configuration, the user can click one button or select one option to save a configuration for later use. Thus, the system can provide a suggestion for a hanging protocol and the user can apply or modify (and cause the system to learn) that suggested layout.

Figure 12:
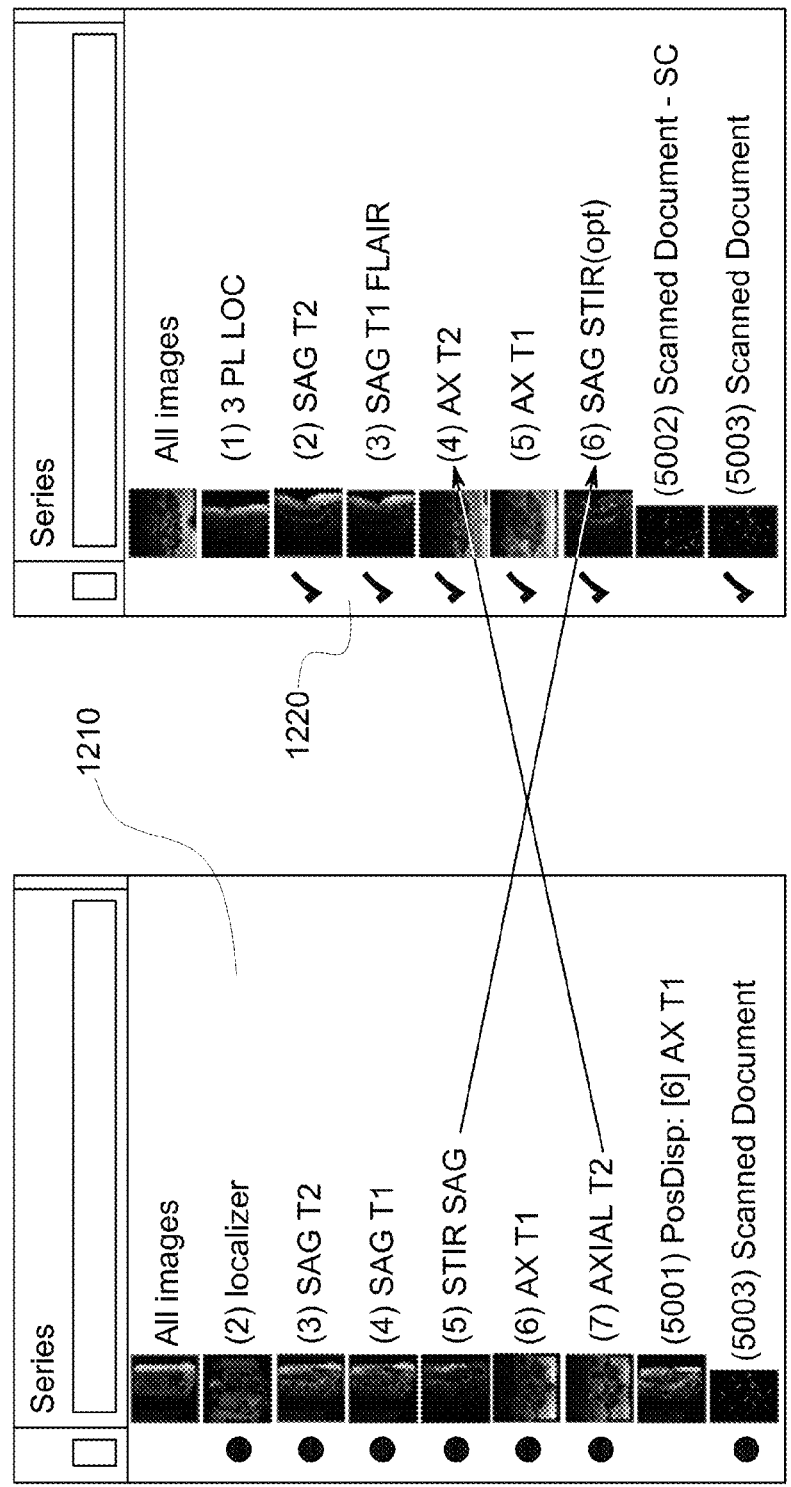

As shown in FIG. 12, differences between series names and order can be learned by the system in response to machine learning and user triggering. For example, STIR SAG is number 5 in a first series 1210 but number 6 with a slightly different name in a second series 1220 while AXIAL T2 is number 7 in the first series but number 4 and named AX T2 in the second series.

Figure 13:
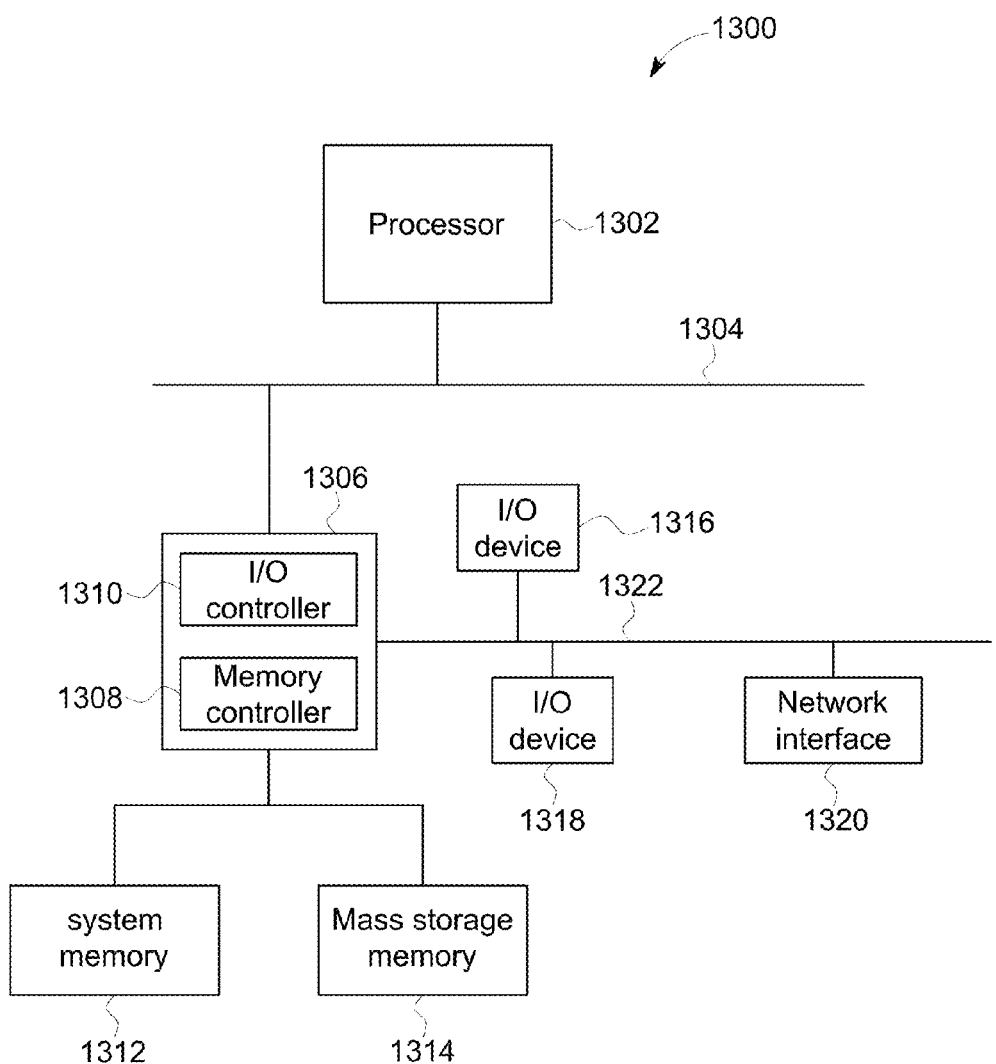
FIG. 13 is a block diagram of an example processor system that may be used to implement the systems, apparatus and methods described herein.

FIG. 13 is a block diagram of an example processor system 1300 that may be used to implement the systems, apparatus and methods described herein. As shown in FIG. 13, the processor system 1300 includes a processor 1302 that is coupled to an interconnection bus 1304. The processor 1302 may be any suitable processor, processing unit or microprocessor. Although not shown in FIG. 13, the system 1300 may be a multi-processor system and, thus, may include one or more additional processors that are identical or similar to the processor 1302 and that are communicatively coupled to the interconnection bus 1304.

The processor 1302 of FIG. 13 is coupled to a chipset 1306, which includes a memory controller 1308 and an input/output (I/O) controller 1310. As is well known, a chipset typically provides I/O and memory management functions as well as a plurality of general purpose and/or special purpose registers, timers, etc. that are accessible or used by one or more processors coupled to the chipset 1306. The memory controller 1308 performs functions that enable the processor 1302 (or processors if there are multiple processors) to access a system memory 1312 and a mass storage memory 1314.

The system memory 1312 may include any desired type of volatile and/or non-volatile memory such as, for example, static random access memory (SRAM), dynamic random access memory (DRAM), flash memory, read-only memory (ROM), etc. The mass storage memory 1314 may include any desired type of mass storage device including hard disk drives, optical drives, tape storage devices, etc.

The I/O controller 1310 performs functions that enable the processor 1302 to communicate with peripheral input/output (I/O) devices 1316 and 1318 and a network interface 1320 via an I/O bus 1322. The I/O devices 1316 and 1318 may be any desired type of I/O device such as, for example, a keyboard, a video display or monitor, a mouse, etc. The network interface 1320 may be, for example, an Ethernet device, an asynchronous transfer mode (ATM) device, an 802.11 device, a DSL modem, a cable modem, a cellular modem, etc. that enables the processor system 1300 to communicate with another processor system.

While the memory controller 1308 and the I/O controller 1310 are depicted in FIG. 13 as separate blocks within the chipset 1306, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN), a wide area network (WAN), a wireless network, a cellular phone network, etc., that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method to determine a hanging protocol for clinical image display, said method comprising:
monitoring, using a processor, user workflow in a first session;
accepting, using a processor, user input to learn at least a portion of the workflow for repeat setup in a second session;
developing a set of user preferences based on the monitoring and the user input; and
applying one or more machine learning algorithms to the developed set of user preferences to develop one or more candidate layouts for selection and application as a hanging protocol.

2. The method of claim 1, further comprising creating a snapshot of a layout and associated parameters to form a layout candidate for a hanging protocol.

3. The method of claim 1, further comprising facilitating user modification of a saved workflow element in a saved hanging protocol.

4. The method of claim 1, further comprising automatically adapting the hanging protocol based on a stored user layout of images.

5. The method of claim 1, further comprising outputting a hanging protocol including one or more parameters to generate a layout for display of images.

6. The method of claim 1, wherein the one or more machine learning algorithms comprises at least one of a lazy learning algorithm, a case based learning algorithm, and an eager learning algorithm.

7. The method of claim 1, further comprising applying image processing in addition to the one or more machine learning algorithms.

8. A non-transitory computer-readable storage medium including a set of instructions for execution by a processor, the instructions, when executed, to implement a method to determine a hanging protocol for clinical image display, said method comprising:
monitoring user workflow in a first session;
accepting user input to learn at least a portion of the workflow for repeat setup in a second session;
developing a set of user preferences based on the monitoring and the user input; and
applying one or more machine learning algorithms to the developed set of user preferences to develop one or more candidate layouts for selection and application as a hanging protocol.

9. The computer-readable medium of claim 8, further comprising creating a snapshot of a layout and associated parameters to form a layout candidate for a hanging protocol.

10. The computer-readable medium of claim 8, further comprising facilitating user modification of a saved workflow element in a saved hanging protocol.

11. The computer-readable medium of claim 8, further comprising automatically adapting the hanging protocol based on a stored user layout of images.

12. The computer-readable medium of claim 8, further comprising outputting a hanging protocol including one or more parameters to generate a layout for display of images.

13. The computer-readable medium of claim 8, wherein the one or more machine learning algorithms comprises at least one of a lazy learning algorithm, a case based learning algorithm, and an eager learning algorithm.

14. The computer-readable medium of claim 8, further comprising applying image processing in addition to the one or more machine learning algorithms.

* * * * *